US012753379B2

(12) United States Patent
Yamamoto

(10) Patent No.: US 12,753,379 B2
(45) Date of Patent: Oct. 6, 2026

(54) AUTOMATIC ANALYSIS SYSTEM

(71) Applicant: Shimadzu Corporation, Kyoto (JP)

(72) Inventor: Kohei Yamamoto, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 1064 days.

(21) Appl. No.: 16/756,225

(22) PCT Filed: Dec. 5, 2017

(86) PCT No.: PCT/JP2017/043588

§ 371 (c)(1),
(2) Date: Apr. 15, 2020

(87) PCT Pub. No.: WO2019/111310

PCT Pub. Date: Jun. 13, 2019

(65) Prior Publication Data

US 2021/0147786 A1 May 20, 2021

(51) Int. Cl.

*G01N 35/00* (2006.01)
*C12M 1/34* (2006.01)

(Continued)

(52) U.S. Cl.

CPC ............ *C12M 41/48* (2013.01); *C12M 41/32* (2013.01); *G01N 35/00871* (2013.01); *G01N 35/025* (2013.01); *G01N 2035/0091* (2013.01)

(58) Field of Classification Search

CPC . C12M 41/48; C12M 41/32; G01N 35/00871; G01N 35/025; G01N 2035/0091; G01N 2035/009

See application file for complete search history.

(56) References Cited

U.S. PATENT DOCUMENTS

2012/0322139 A1* 12/2012 Nogami ............. G01N 35/0098 422/68.1
2013/0009988 A1* 1/2013 Tokunaga ........ G01N 35/00871 345/660

(Continued)

FOREIGN PATENT DOCUMENTS

CN 102483423 A 5/2012
EP 2485054 A1 8/2012

(Continued)

OTHER PUBLICATIONS

First Office Action dated Jan. 5, 2023 issued for the corresponding Chinese Patent Application No. 201780096895.5.

(Continued)

*Primary Examiner* — Melvin C. Mayes
*Assistant Examiner* — Sophia Y Lyle
(74) *Attorney, Agent, or Firm* — Muir Patent Law, PLLC

(57) ABSTRACT

On a device state confirmation screen (100), a first sample arrangement image (111) showing a top-view image of a sample placement section in a preprocessing device for performing preprocessing of removal of proteins or the like and a second sample arrangement image (121) showing a top-view image of a sample placement section of an auto-sampler of an LC-MS are simultaneously displayed. In the respective sample arrangement images (111, 121), a placement position of a vial is indicated by a circular region (113, 122), and the same vial number A1, A2, . . . , is assigned to a vial in which one culture medium sample is accommodated and a vial in which a preprocessed sample is accommodated. Further, circular regions 113 and 122 are displayed in different display colors depending on a state of progress of the preprocessing operation and the analysis operation. As a result, an operator can visually recognize easily and assuredly the correspondence relationship between positions of a large number of vials placed in the sample placement (Continued)

section and positions of a large number of vials accommodating preprocessed samples placed in the auto-sampler, which prevents erroneous selection of samples.

8 Claims, 12 Drawing Sheets

(51) Int. Cl.
*C12M 1/36* (2006.01)
*G01N 35/02* (2006.01)

(56) References Cited

U.S. PATENT DOCUMENTS

| | | | | |
|---|---|---|---|---|
| 2016/0139166 | A1* | 5/2016 | Berberich | G01N 35/1016 435/6.12 |
| 2016/0238623 | A1* | 8/2016 | Sun | G01N 21/6428 |
| 2017/0052171 | A1 | 2/2017 | Suzuki et al. | |
| 2017/0176480 | A1* | 6/2017 | Moschell | G01N 35/00722 |
| 2019/0119650 | A1 | 4/2019 | Suzuki et al. | |

FOREIGN PATENT DOCUMENTS

| | | | | |
|---|---|---|---|---|
| JP | 2010-190779 | A | 9/2010 | |
| JP | 2016-170079 | A | 9/2016 | |
| JP | 2017-170079 | A | 9/2017 | |
| WO | WO-0138882 | A1 * | 5/2001 | G01N 35/025 |
| WO | WO-2011037069 | A1 * | 3/2011 | G01N 35/00871 |
| WO | WO-2013016038 | A1 * | 1/2013 | G01N 15/1429 |
| WO | 2015/166845 | A1 | 11/2015 | |
| WO | 2017/068727 | A1 | 4/2017 | |
| WO | 2017/068801 | A1 | 4/2017 | |

OTHER PUBLICATIONS

Written Opinion of the International Searching Authority (ISA237) for PCT application PCT/JP2017/043588, dated Feb. 20, 2018, submitted with a machine translation.

"LC/MS/MS Method Packaged Cell Culture Profiling," [online], [Searched on Nov. 21, 2017], Shimadzu Corporation, Internet <URL: http://www.an.shimadzu.co.jp/lcms/tq-option/mp_profiling_cell-culture.htm> submitted with a machine translation.

"SCLAM-2000 Fully Automated LCMS preprocessing device," [online], [Searched on Nov. 21, 2017], Shimadzu Corporation, Internet <URL: http://www.an.shimadzu.co.jp/lcms/sclam2000-2.htm> with a partial translation.

Notice of Allowance dated Aug. 30, 2023 issued for the corresponding Chinese Patent Application No. 201780096895.5.

* cited by examiner

AUTOMATIC ANALYSIS SYSTEM

TECHNICAL FIELD

The present invention relates to an automatic analysis system for performing a predetermined preprocessing on a sample and analyzing the preprocessed sample. This automatic analysis system is particularly suitable for analyzing a biological sample containing biological origin compounds. The biological sample described herein includes whole blood, sera, filtered paper blood, urine, and the like, as well as culture supernatant containing various types of metabolites obtained from a culture medium for culturing various types of cells such as, e.g., pluripotent stem cells.

BACKGROUND OF THE INVENTION

In the field of regenerative medicine, researches and technological developments using pluripotent stem cells, such as, e.g., iPS cells and ES cells, have been actively carried out in recent years. In such researches and technological developments, it is necessary to culture large quantities of undifferentiated cells in a state in which pluripotency is maintained. Therefore, it is necessary to select an appropriate cultural environment and stably control the environment, and it is also necessary to confirm the state of cells in culture at a high frequency.

For example, if cells within a cell colony deviate from an undifferentiated state, all cells within the cell colony will eventually transition to undifferentiated deviant states because all cells within the cell colony are capable of differentiating. Therefore, the operator needs to check daily whether or not cells that deviated from the differentiation state (cells that have already differentiated or are likely to differentiate) are generated in the cultured cells, that is, the differentiation state of the cells.

Conventionally, as a method for evaluating the differentiation state of cells, a method using immunostaining or a method for quantifying the expression levels of marker genes has been widely used. However, all of these methods require invasive treatment of the cells. Therefore, it has not been possible to use the cells used for the evaluation after the evaluation of differentiation state for another purpose, for example, as a cell source for regenerative medicine. It was also impossible to evaluate changes over time for completely identical samples.

On the other hand, Patent Documents 1 to 3 disclose methods for analyzing the abundance of a particular compound in a culture supernatant of a culture medium culturing a cell, not the cell itself, by using a liquid chromatograph mass analysis device (LC-MS) or a gas chromatograph mass analysis device (GC-MS), and evaluating the differentiation state of the cell based on the result. Software for an LC-MS to perform culture medium analyses to culture cells has also been put into practical use to perform such methods (see Non-Patent Document 1). Such methods have a significant benefit that the differentiation state of the cells can be assessed non-invasively with respect to the cells.

In evaluating the differentiation state of cells based on the analytical results of the particular compounds in the culture supernatant described above, after sample cells are cultured in a culture medium, a sample (culture medium sample) derived from the culture medium used for the culture is introduced from the culture device into an analysis device, such as, a liquid chromatograph mass analysis device. However, a culture medium sample also includes a protein that is not necessary for evaluating the differentiation state of the cells and that may denature the target compound over time. Therefore, generally, a culture medium sample after preprocessing such as removing proteins is performed in a preprocessing device is introduced into an LC-MS. That is, the culture medium sample is introduced from a culture device to an analysis device, such as, e.g., an LC-MS, through a preprocessing device. As a preprocessing device, a device capable of automatically and sequentially processing a large number of samples contained in sample containers, which is disclosed in, for example, Patent Document 4 and Non-Patent Document 2, and the like, is usable.

PRIOR ART DOCUMENT

Patent Document

Patent Document 1: Re-published WO 2015/166845 Bulletin

Patent Document 2: International Publication No. 2017/068727 Pamphlet

Patent Document 3: International Publication No. 2017/068801 Pamphlet

Patent Document 4: Japanese Unexamined Patent Application Publication No. 2017-170079

Non-Patent Document

Non-Patent Document 1: "LC/MS/MS Method Packaged Cell Culture Profiling, [online], [Searched on Nov. 21, 2017], Shimadzu Corporation, Internet <URL: http://www.an.shimadzu.co.jp/lcms/tq-option/mp_profiling_cell-culture.htm>

Non Patent Document 2: "SCLAM-2000 Fully Automated LCMS preprocessing device, [online], [Searched on Nov. 21, 2017], Shimadzu Corporation, Internet <URL: http://www.an.shimadzu.co.jp/lcms/sclam2000-2.htm>

SUMMARY OF THE INVENTION

Problems to be Solved by the Invention

As disclosed in Patent Document 4 and the like, the above-mentioned preprocessing device has a configuration in which one of a number of sample containers placed in a sample placement section in advance is selected, predetermined preprocessing is performed in a sample accommodated in the sample container, and a container accommodating the processed sample is transferred to a position that can be handled by a next-stage analysis device. When performing a batch analysis in which a number of samples are sequentially analyzed by an analysis device such as an LC-MS is performed after preprocessing of a number of samples in such a preprocessing device, many sample containers containing preprocessed samples are placed in a sample placement section of an auto-sampler in which one of many samples is selected in the LC-MS and the selected sample is introduced to the LC-MS.

That is, a large number of sample containers are placed in the sample placement section of the preprocessing device, and a large number of sample containers are also placed in the sample placement section of the auto-sampler of the LC-MS. Depending on the specifications of the device, the number of sample containers placed in each sample placement section may be close to one hundred or more. Which sample placement section of preprocessing device of the auto-sampler of the LC-MS the preprocessed sample obtained by preprocessing a sample in the sample container placed at a certain position in the sample placement section of the preprocessing device is placed is uniquely determined since it is determined by the programs controlling the operation of the preprocessing device and the auto-sampler. However, since the number of sample containers is large in each sample placement section as described above, it is difficult for an operator to grasp the correspondence relationship between the position of the sample container in the sample placement section in the preprocessing device and the position of the sample container in the sample placement section of the auto-sampler of the LC-MS.

For example, in cases where a sample is analyzed and it is found in the sample placement section of the auto-sampler that the state of the sample placed at a certain position is poor (e.g., cells have already differentiated), it may be desired to discard not only preprocessed samples but also samples that have not been subjected to preprocessing. However, if an operator incorrectly recognizes the correspondence relationship between the position of the sample containers in the sample placement section in the preprocessing device and the position of the sample containers in the sample placement section in the auto-sampler of the LC-MS, the samples to be left may be incorrectly discarded.

In some cases, it is desired to selectively analyze samples of a particular culturing condition (culture name, seeding date and time, collection date and time, etc.) from among a large number of samples placed in the sample placement section of the auto-sampler, but if the correspondence relationship between the position of the sample container in the sample placement section of the preprocessing device and the position of the sample container in the sample placement section of the auto-sampler of the LC-MS cannot be easily grasped, it takes time and labor to select a target sample.

The present invention has been made to solve the above-mentioned problems, and an object thereof is to provide an automatic analysis system capable of easily and accurately grasping a correspondence relationship between a position of a sample container in a sample placement section of a preprocessing device and a position in a sample placement section of an analysis device in which a sample container in which a sample after preprocessing the sample in the container is accommodated or is to be accommodated is placed.

Means for Solving the Problem

According to the present invention made to solve the aforementioned problems, an automatic analysis system for performing predetermined preprocessing on a sample and then performing a predetermined analysis on a preprocessed sample, includes:

a) a preprocessing device having a sample placement section for placing a plurality of sample containers each containing a sample, the preprocessing device being configured to perform preprocessing on the sample in the sample container placed in the sample placement section;

b) a preprocessed sample delivering unit configured to deliver a container for temporality accommodating the sample to which the preprocessing by the preprocessing device has been completed to a predetermined position of an analysis device described later;

c) an analysis device having a sample placement section for placing a plurality of sample containers for accommodating the preprocessed sample in the container delivered to the predetermined position by the preprocessed sample delivering, the analysis device being configured to perform an analysis on the preprocessed sample in the sample container placed in the sample placement section of the analysis device;

d) a sample container identifier management unit configured to manage to allocate a same sample container identifier to one sample container in the sample placement section of the preprocessing unit and a sample container placed in the sample placement section of the analysis device in a state in which the preprocessed sample which is a sample accommodated in the one sample container and preprocessed is accommodated therein; and e) a display processing unit configured to display a first sample arrangement image showing an arrangement state of a plurality of sample containers in the sample placement section of the preprocessing device and a second sample arrangement image showing an arrangement state of a plurality of sample containers in the sample placement section of the analysis device in different regions on a same screen, and display the same sample container identifier with respect to display regions of sample containers in which samples derived from the same sample are accommodated in a display region corresponding to each sample container in the first sample placement image and in a display region corresponding to each sample container in the second sample placement image, according to a management by the sample container identifier management unit.

The analytical method in the analysis device according to the present invention is not particularly limited, but the analysis device is exemplified by a liquid chromatograph (LC), a gas chromatograph (GC), a liquid chromatograph mass analysis device (LC-MS, a gas chromatograph mass analysis device (GC-MS), and the like. Although the contents of preprocessing in the preprocessing device are not particularly limited, for example, when a sample is a biological sample, the preprocessing may be a process of removing various components (e.g., proteins) which hinder the analysis. The biological sample referred to herein may be a sample itself taken from a living body such as blood, and also may be a culture medium sample containing components from cells or living tissues when culturing the cells or living tissues as described above.

In the present invention, prior to the analysis, a number of sample containers each containing a biological sample such as a culture medium sample are prepared in a sample placement section of a preprocessing device. The sample container is, for example, a vial. In this case, the sample placement section is, for example, a rack in which a recess is formed in which the bottom of the vial is accommodated. When the preprocessing is started, the preprocessing device sequentially executes preprocessing on a sample in a prepared sample container. For example, the sample that preprocessing has been completed is once accommodated in a container different from the sample container, and the container is transferred to a predetermined position of an analysis device.

In the analysis device, a predetermined quantity of the preprocessed sample is aspirated from a container transferred to a predetermined position and injected into a sample container (a sample container different from the sample container used for preprocessing) placed on a sample placement unit of the analysis device. In this case, dilution or the like may be performed. By repeating this operation, in the sample containers placed in the sample placement section of the analysis device, preprocessed samples different from each other are accommodated. The analysis device sequentially executes an analysis on the preprocessed samples in the sample containers, and acquires the analysis result for each sample. For example, when the analysis device is an LC-MS, the analytical result is extracted ion chromatogram (also referred to as a mask chromatogram) data in a predetermined time-span at one or more mass-to-charge ratios.

The sample container identifier management unit allocates identifiers so that the same identifier is allocated to samples derived from the same sample for a sample container identifier of each sample container placed in the sample placement section of the preprocessing device and a sample container identifier of each sample container placed in the sample placement section of the analysis device, and manages the allocation information. The sample container identifier is typically a sample container number, but may be any suitable symbol or code.

In response to a predetermined manipulation of an operator at any time, such as, e.g., prior to, during, or after the analysis, the display processing unit creates a screen in which a first sample arrangement image indicating the arrangement state of a plurality of sample containers in the sample placement section of the preprocessing device and a second sample arrangement image indicating the arrangement state of a plurality of sample containers in the sample placement section of the analysis device are arranged in different regions on the same screen, and displays the screen on a display unit. At this time, the same identifier is displayed on display regions corresponding to two sample containers, i.e., a sample container in which a sample before preprocessing is accommodated and a sample container in which the same sample after preprocessing is accommodated for a display region corresponding to each sample container in the first sample arrangement image and a display region corresponding to each sample container in the second sample arrangement image, based on the management information of the identifier by the sample container identifier management unit.

With this, the arrangement state of the sample containers in the sample placement section of the preprocessing device and the arrangement state of the sample containers in the sample placement section of the analysis device are displayed on the same screen. Then, in the first sample arrangement image and the second sample arrangement image indicating the arrangement state of the sample containers in each sample placement section, the same sample container identifier is given to the display region corresponding to the sample containers in which certain samples are accommodated and the display region corresponding to the sample containers in which preprocessed samples are accommodated. Therefore, an operator can easily and assuredly grasp the correspondence relationship of the positions of the sample containers in both the sample placement sections from the sample container identifier.

Also in the present invention, preferably, the display processing unit is configured to receive information indicating a state of progress of respective operations from the preprocessing device and the analysis device and change a display mode in the display region corresponding to each sample container in the first sample arrangement image and a display mode in the display region corresponding to each sample container in the second sample arrangement image, according to the state of progress.

The change of display mode is typically a change of display color, but the type and thickness of the line indicating the display region may be changed. Alternatively, the display color, the type of fonts or the like of the sample container number corresponding to the display region may be changed.

According to this configuration, the operator can easily and accurately grasp the state of progress of the preprocessing operation and the state of progress of the analytical operation on one screen.

Further, in the present invention, the automatic analysis system further includes:

- a display region identification unit configured for a user to identify one or more display regions corresponding to respective sample containers in the first sample arrangement image;
- a sample information setting screen display processing unit included in the display processing unit and configured to display an input setting screen which allows a user to input information of a sample accommodated in the sample container associated with one or more display regions when the one or more display regions are identified via the display region identification unit; and
- a sample information acquisition unit configured to store sample information input by an operation of the user on an input setting screen displayed by the sample information setting screen display processing unit in association with the sample container identifier.

The contents of the sample information described here differ depending on the type of the sample. For example, when a sample is a culture medium sample derived from a culture medium in which cells are cultured as described above, the sample information may include at least one of a culture name, a seeding date and time, a sample collection date and time, a culture plate number, and the like. According to this configuration, the operator can input and set the sample information by a simple operation on the screen on which the state of progress of the operation of preprocessing and the state of progress of the operation of the analysis can be confirmed.

When inputting and setting the sample information, it is more convenient to know at a glance on the first sample arrangement image whether or not the sample information has not been set or the sample information has been set for each sample container in the sample placement section of the preprocessing device.

Therefore, in the present invention, preferably, the display processing unit is configured to change the display mode of the display region corresponding to each sample container in the first sample arrangement image depending on whether or not the sample information has been set

Effects of the Invention

According to the present invention, the correspondence relationship between the position of the sample container in the sample placement section of the preprocessing device and the position of the sample container in the sample placement section of the analysis device in which the preprocessed sample which is a sample contained in the sample container and preprocessed is contained can be easily and accurately grasped visually. Thereby, even in cases where, for example, an operator manually selects and analyzes a sample or collects a sample, it is possible to prevent a sample from being mistakenly used, which can improve the operation efficiency.

EMBODIMENTS FOR CARRYING OUT THE INVENTION

Hereinafter, a culture medium sample automatic analysis system, which is an example of an automatic analysis system according to the present invention, will be described in detail with reference to the attached drawings.

Figure 1:
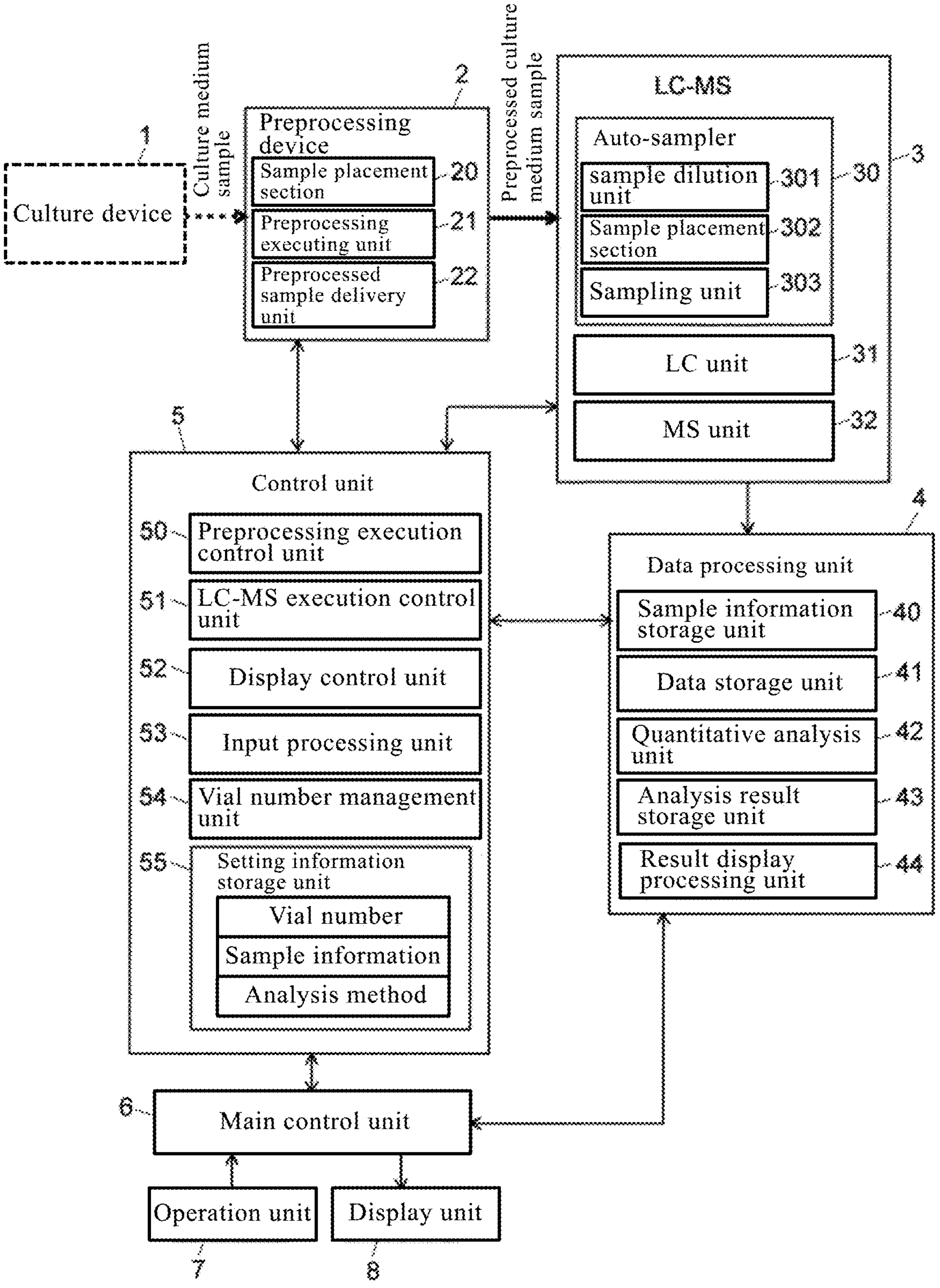
FIG. 1 is a schematic block configuration diagram of a culture medium sample automatic analysis system which is an example of the present invention.

FIG. 1 is a schematic block diagram of a culture medium sample automatic analysis system of this example. The system of this example is a cultured cell evaluation system that is used to assess the differentiation state of sample cells based on the abundance of biomarker (cellular metabolite) in a culture supernatant of a culture medium in which sample cells, such as pluripotent cells, are cultured.

The system of this example is provided with a preprocessing device 2, a liquid chromatograph mass analysis device (LC-MS) 3, a data processing unit 4, a control unit 5, a main control unit 6, an operation unit 7, a display unit 8, etc. The culture device 1 in the block shown by the dotted line in FIG. 1 is not included in this system, and provides a culture medium sample to be analyzed by this system.

Schematically, in this system, a number of culture medium samples obtained in the culture device 1 are provided to the preprocessing device 2. In the preprocessing device 2, predetermined preprocessing is sequentially performed for a number of culture medium samples. Then, each culture medium sample (preprocessed sample) that preprocessing has been performed by the preprocessing device 2 is sent to the LC-MS 3. The components in each culture medium sample are sequentially analyzed in the LC-MS 3. The analytically obtained data is sent to the data processing unit 4, and the data processing unit 4 performs predetermined data processing and outputs the result to the display unit 8 via the main control unit 6 for presentation to a user (operator). The control unit 5 controls the preprocessing device 2, the LC-MS 3, and the data processing unit 4 for the aforementioned processing. The main control unit 6 mainly has a function of a user interface through the operation unit 7 and the display unit 8.

The configuration of each unit will be described in detail.

The culture device 1 is a device for culturing sample cells. Here, the sample cells are, for example, stem cells, typically pluripotent cells, such as, e.g., ES cells and iPS cells. Cells differentiated from stem cells can also be used as sample cells. As a culture medium used for culturing such sample cells, various culture mediums commonly used for culturing stem cells, such as DMEM/F12 or a culture medium (mTeSR1) containing DMEM/F12 as the main component, can be used. When cells are cultured on such a culture medium, various types of metabolites by cells are mixed in the culture supernatant. An operator prepares a culture medium sample by manually collecting a part of culture supernatant and injecting it into a predetermined vial (sample container). Of course, a part of culture supernatant may be automatically collected at a fixed time every day, i.e., a culture medium sample may be automatically prepared.

The preprocessing device 2 is provided with: a sample placement section 20 including a sample rack on which a plurality of vials is placed; a preprocessing executing unit 21 which executes preprocessing for removing unwanted components such as proteins through processes of sample dispensing, reagent dispensing, agitation, filtration, and the like, with respect to a culture medium sample in one vial selected from a plurality of vials placed in the sample placement section 20; and a preprocessed sample delivery unit 22 which transfers a container in which a culture medium sample that preprocessing has been completed is temporarily stored to a predetermined position of the LC-MS 3.

In this example, as will be described later, the sample rack used in the preprocessing device 2 has a substantially circular arc shape in a top view, and six pieces of sample racks are arranged in the sample placement section 20 along the circumferential direction of the circular ring. Ten or eleven vials can be placed on one sample rack. That is, each sample rack is provided with concave portions each having a size capable of accommodating a bottom portion of each of the plurality of vials, and each vial can be placed in each concave portion.

More specifically, in the preprocessing of removing proteins, isopropyl malic acid as an internal standard sample is added to a culture medium sample as a reagent, and can be processed with an extracting solution in which methanol, chloroform, and water are mixed in a ratio of 2.5:1:1, for example. However, the preprocessing is not limited to removal of proteins, and other preprocessing may be performed on a culture medium sample. As the preprocessing device 2, for example, a device disclosed in Patent Document 4, Patent Document 2, or the like can be used, but the present invention is not limited thereto.

The LC-MS 3 includes a liquid chromatograph (LC) unit 31 including a liquid feed pump, an injector, a column, and the like (not shown), an auto-sampler 30 for selecting one of a plurality of culture medium samples and introducing it into the LC unit 31, and a mass spectrometry (MS) unit 32 for performing mass spectrometry on components in a sample separated in a temporal direction by a column of the LC unit 31. The auto-sampler 30 includes a sample placement section 302 including a sample rack on which a number of vials differing from those used in the preprocessing device 2 are placed, a sample dilution unit 301 for aspirating a preprocessed culture medium sample in a container transferred to a predetermined position by a preprocessed sample delivery unit of the preprocessing device 2, adding ultrapure water to dilute it to a predetermined ratio, and then dispensing it to a vial placed in a sample placement section 302, and a sampling unit 303 for collecting a preprocessed and diluted culture medium sample by a predetermined amount from a sample delivery unit 22 of one of a number of vials placed in the sample placement section 302 and introducing it into an injector of the LC unit 31.

In this example, as will be described later, the sample rack used in the auto-sampler 30 has a rectangular shape in a top view, and vials can be arranged in a matrix of n rows and m columns (12 rows and 8 columns in this example) in one sample rack.

In order to evaluate the differentiation state of the sample cell, mass spectrometry is performed in the MS unit 32 on at least one target compound selected from the group consisting of, for example, putrescine, quinurenin, cystathionine, ascorbic acid, riboflavin, pyruvic acid, serine, cysteine, threonic acid, citric acid, and orotic acid as a biomarker. The method of the mass analysis device used as the MS unit 32 is not particularly limited as long as it includes an atmospheric pressure ion source, and for example, a quadrupole mass analysis device, a tandem quadrupole mass analysis device, a quadrupole-time-of-flight mass analysis device, or the like can be used.

The data processing unit 4 includes functional blocks, such as, e.g., a sample information storage unit 40, a data storage unit 41, a quantitative analysis unit 42, an analysis result storage unit 43, and a result display processing unit 44. The sample information storage unit 40 stores the sample information input and set for each vial in which a culture medium sample is accommodated in the preprocessing device 2, as will be described later. The data storage unit 41 stores the data collected by performing analyses in the LC-MS 3. The quantitative analysis unit 42 creates an extracted ion chromatogram for each data obtained by targeting a particular compound, uses the calibration curve created in advance, and calculates the concentration value of the compound based on the area value and the height value of the peaks observed in the chromatogram. The analysis result storage unit 43 stores the result of computation by the quantitative analysis unit 42 or the like. The result display processing unit 44 prepares a graph based on the calculated analytical result and the like, prepares a screen of a predetermined format in which the graph is arranged, and outputs the screen to the display unit 8 via the main control unit 6.

The control unit 5 includes functional blocks, such as, e.g., a preprocessing execution control unit 50, an LC-MS execution control unit 51, a display control unit 52, an input processing unit 53, a vial number management unit 54, and a setting information storage unit 55. The preprocessing execution control unit 50 controls the preprocessing operation in the preprocessing device 2. The LC-MS execution control unit 51 controls the analysis operation in the LC-MS 3. As will be described later, the display control unit 52 creates a screen for displaying the operating states of the preprocessing device 2 and the LC-MS 3, or a screen for setting the information (sample information) of a culture medium sample used for the preprocessing device 2 or the analytical condition for the respective samples by an operator, and outputs the screen to the display unit 8 via the main control unit 6. The input processing unit 53 executes a predetermined process in response to an input operation of the operation unit 7 by an operator. The vial number management unit 54 assigns a vial number to a vial position in each of the sample placement section 20 and the sample placement section 302 according to a predetermined rule or according to a manual setting by a user, and manages the assigned information. The setting information storage unit 55 stores the sample information, the analysis condition, and the like of each culture medium sample, which are input and set by input operations by an operator or the like.

Note that the data processing unit 4, the control unit 5, and the main control unit 6 are personal computers (or more sophisticated workstations), and the functions of the above-mentioned blocks can be achieved by operating one or a plurality of dedicated software installed in the computer on the computer. In this configuration, the operation unit 7 is a keyboard or a pointing device such as a mouse attached to a personal computer or the like, and the display unit 8 is a display monitor.

As described above, in this system, a culture medium sample contained in one vial among a plurality of vials to be placed in the sample placement section 20 in the preprocessing device 2 is subjected to preprocessing and a diluting operation and injected into one vial among a plurality of vials placed in a sample placement section 302 of the auto-sampler 30. Therefore, in principle, a large number of vials placed in the sample placement section 20 in the preprocessing device 2 and a large number of vials placed in the sample placement section 302 in the auto-sampler 30 can be associated one-to-one. The characteristic display control is performed so that an operator can easily and accurately grasp the correspondence relationship between the vials. Next, the display control will be described.

Figure 2:
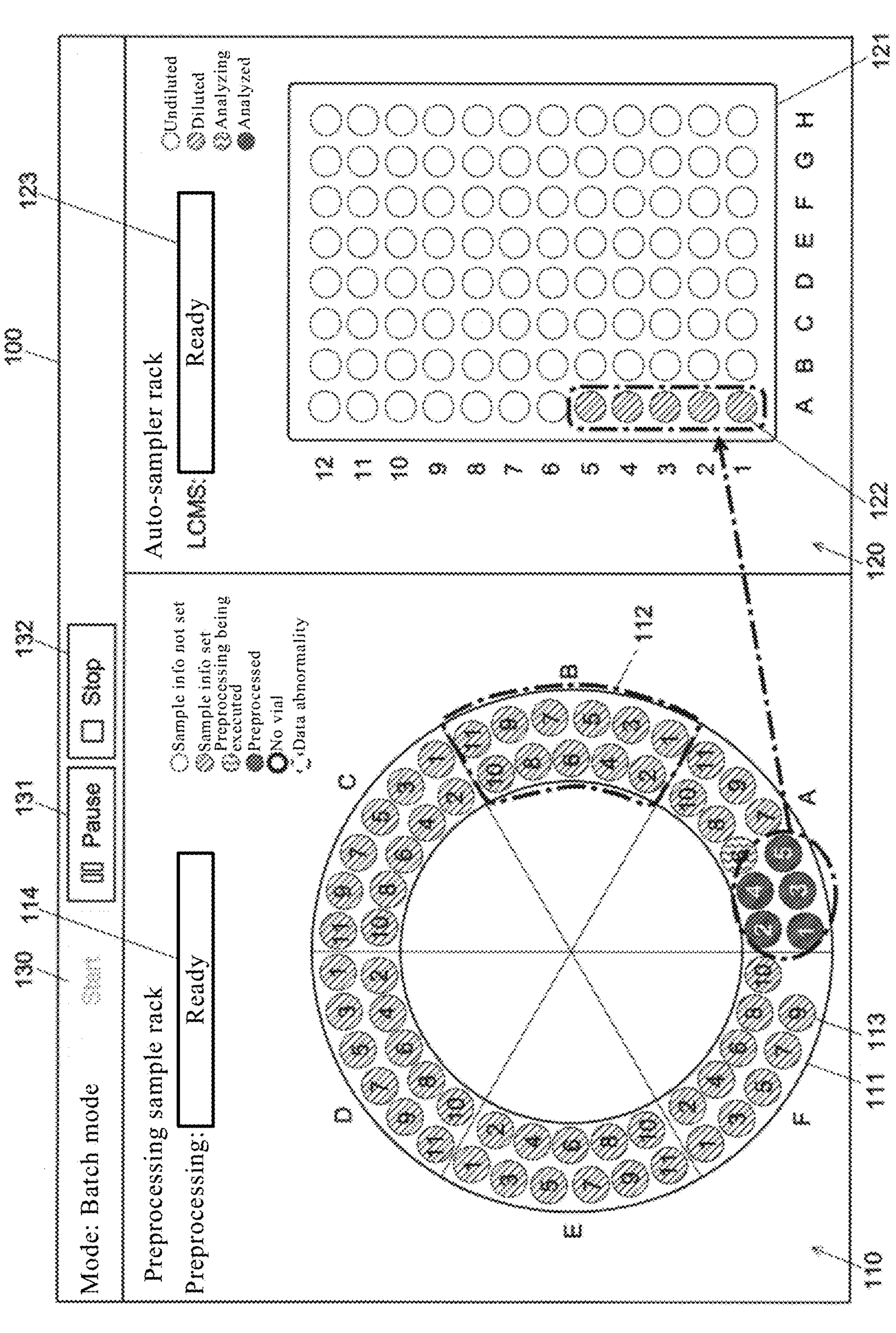
FIG. 2 is a schematic diagram showing an example of a device status display screen displayed on a display unit in the culture medium sample automatic analysis system of this example.

When an operator performs a predetermined manipulation on the operation unit 7, the display control unit 52, which has received the instruction via the main control unit 6, creates a device state confirmation screen in a predetermined format and displays it on the screen of the display unit 8. FIG. 2 is a schematic diagram showing an example of the device state confirmation screen 100. This device state confirmation screen 100 is a screen for displaying the information on the operation of the preprocessing device 2 and the information on the operation of the LC-MS 3 at the same time. That is, the device state confirmation screen 100 is generally divided into two parts on the left and right, and the left side is a preprocessing state display region 110 and the right side is an analysis state display region 120.

In the preprocessing state display region 110 of the device state confirmation screen 100, a first sample arrangement image 111 graphically showing the top-view image of the sample placement section 20 in the preprocessing device 2 is displayed. This first sample arrangement image 111 is divided into six pieces of arcuate regions 112 in association with six pieces of substantially arc-shaped sample racks arranged along the circumference of the circular ring in the same manner as in the actual sample placement section 20, and each arcuate region 112 thereof is provided with circular regions 113 corresponding to a plurality (11 pieces) of vials in this embodiment.

Here, as shown in FIG. 2, the letters “A”, “B”, “C”, “D”, “E”, and “F” are given to the six arcuate regions 112, respectively, as region names. In addition, a plurality of circular regions 113 in each arcuate region 112 is given by numbers which are consecutive numbers of “1” to “11”. All of the circular regions 113 in the first sample arrangement image 111 are identified by a vial number in which an alphabetic character showing the arcuate region 112 to which the circular region 113 belongs and a number which is a sequence number in the arcuate region 112 are combined. To the vial placed in a position corresponding to the circular region 113, its vial number is assigned as a sample container identifier. The relationship between the position of the vial and the vial number in the sample placement section 20 is managed by the vial number management unit 54.

The display color of each circular region 113 indicates the status of executing the preprocessing on the culture medium sample in the vial at the position corresponding to the circular region 113. Specifically, the execution status of preprocessing represented here includes six types of execution statuses, such as "sample information not set" in which sample information such as the sample name has not yet been set, "sample information set" in which preprocessing has not yet been executed although sample information has been set, "preprocessing being executed" in which preprocessing is being executed, "preprocessed" in which preprocessing has been completed, "no vial" indicating that a vial does not exist in the position, and "data abnormality" in which the abnormality occurred during preprocessing. However, here, because colors cannot be represented due to the restrictions of the drawings, the execution state of preprocessing and the like are shown by the differences in filling, differences in line types indicating regions, and the like.

In the example of FIG. 2, the circular regions 113 corresponding to the five vials with vial numbers of "A1" to "A5" are in the "preprocessed" state, and the circular region 113 corresponding to the one vial with the vial number of "A6" is in the "preprocessing being executed" state. All other data are in the "sample information set" state.

At the upper portion of the first sample arrangement image 111 in the preprocessing state display region 110, an operating state display unit 114 that indicates the operating condition of the preprocessing device 2 is provided. In this example, "Ready" is displayed on the operating state display unit 114 because preprocessing in the preprocessing device 2 is in a preprocessing completed state capable of executing the preprocessing. However, the display of the operating state display unit 114 is switched such that "Suspended" or the like is displayed when the preprocessing device 2 is suspended and that "Standby" or the like is displayed when the preprocessing device is activated but the preparation has not yet been completed.

On the other hand, on the analysis state display region 120 of the device state confirmation screen 100, a second sample arrangement image 121 graphically showing the top-view image of the sample placement section 302 in the auto-sampler 30 is displayed. The second sample arrangement image 121 is provided with circular regions 122 corresponding to a plurality of vials arranged in a matrix of n rows and m columns (12 rows and 8 columns in this example) in the same manner as in the actual sample placement section 302.

Here, as shown in FIG. 2, alphabetical characters of "A", "B", "C", "D", "E", "F", "G", and "H" are assigned to the respective columns in the second sample arrangement image 121, and numbers which are sequence numbers of "1" to "12" are assigned to the respective rows. All of the circular regions 122 in the second sample arrangement image 121 are identified by a vial number in which an alphabetic character and a number are combined. To the vial at the position in the circular region 122, its vial number is given as a sample container identifier. The relationship between the vial position and the vial number in the sample placement section 302 is also managed by the vial number management unit 54.

The display color of each circular region 122 indicates the status of the diluting operation in the auto-sampler 30 for a preprocessed and diluted culture medium sample in a vial at a position corresponding to the circular region 122, and the status of performing the analysis in the LC unit 31 and the MS unit 32, etc. Specifically, the dilution operation and the execution state of the analysis shown here are four types of "Undiluted" in which the dilution processing has not yet been executed, "Diluted" in which the measurement has not been performed although the dilution processing has been completed, "Analyzing" in which the analysis is being executed, and "Analyzed" in which the analysis has been completed. Of course, here, instead of colors, the dilution operation, the execution state of the analysis, and the like are shown by the difference in filling and the like.

In the example of FIG. 2, the circular regions 122 corresponding to the five vials with the sample numbers of "A1" to "A5" are in the "Diluted" state. The circular regions 122 corresponding to all other vials is in the "Undiluted" state. As described above, in this system, since the diluted culture medium sample is injected into each vial, it means that a culture medium sample has not yet been injected into the vial at a position in which the circular region 122 is in the "Undiluted" state.

An operating state display unit 123 indicating the operating states of the LC unit 31 and the MS unit 32 is provided on the upper portion of the second sample arrangement image 121 in the analysis state display region 120. In this example, "Ready" is displayed on the operating state display unit 123 because the LC unit 31 and the MS unit 32 are ready for operation. However, the operating state display unit 123 is switched such that "Suspended" is displayed when the LC unit 31 and the MS unit 32 are suspended and that "In preparation" when it has been activated but the preparation has not yet been completed.

At the top portion of the device state confirmation screen 100, a start (Start) button 130 operated when the analysis is started, a pause (Pause) button 131 operated when the analysis is paused, and a stop (Stop) button 132 operated when the analysis is stopped are arranged. After selecting an analysis method registered in advance, the analyst can instruct the start of a series of analyses including preprocessing by clicking the start button 130. Note that, FIG. 2 shows that the start button 130 has been operated and the analysis is in progress.

As described above, the vial number management unit 54 manages the relationship between the position and the vial number of the vial placed in the sample placement section 20 of the preprocessing device 2, and also manages the relationship between the vial and the vial number placed in the sample placement section 302 of the auto-sampler 30. Under this control, the vial in the sample placement section 20 and the vial in the sample placement section 302 are associated so that the sample after preprocessing of a vial in the sample placement section 302 of a vial of a vial number placed in the sample placement section 20 of the preprocessing device 2 (actually, a further diluted sample) is dispensed into a vial of the same vial number placed in the sample placement section 302 of the auto-sampler 30. Therefore, in the vial of the position corresponding to the region having the same vial number on the first sample arrangement image 111 and on the second sample arrangement image 121 in the device state confirmation screen 100, it is ensured that the sample from the same culture medium sample is accommodated. Thereby, the operator can easily grasp on the display whether or not the same sample as the sample in the vial placed in one sample placement section 20 or 302 (whether or not preprocessing or dilution has been performed is different) is in a vial placed in the other sample placement section 302 or 20.

Further, it is possible to easily grasp the culture medium sample in a vial placed in each sample placement section 20 and 302 is in which stage of preprocessing or analysis on the display. For example, as shown by a dot-dash line in FIG. 2, the second sample arrangement image 121 can easily recognize that preprocessing in the preprocessing device 2 has been completed for the culture medium samples in the five vials having the vial numbers of "A1" to "A5" in the first sample arrangement image 111 and they have been transferred to the auto-sampler 30 and have been diluted.

In the example shown in FIG. 2, sample information has been set for all vials placed in the sample placement section 20 of the preprocessing device 2, and the analysis has been started. On the other hand, before starting the analysis, the operator inputs and sets the sample information about the culture medium sample in each vial and the analysis condition for analyzing each culture medium sample by the LC-MS4 for all vials placed in the sample placement section 20 of the preprocessing device 2. The sample information includes the seeding date and time, the culture name, the culture plate number, the harvest date and time, etc. The analysis method including the set sample information and the analysis condition is stored in the setting information storage unit 55 in association with the vial number. In one approach, the sample information can be set as follows.

Figure 3:
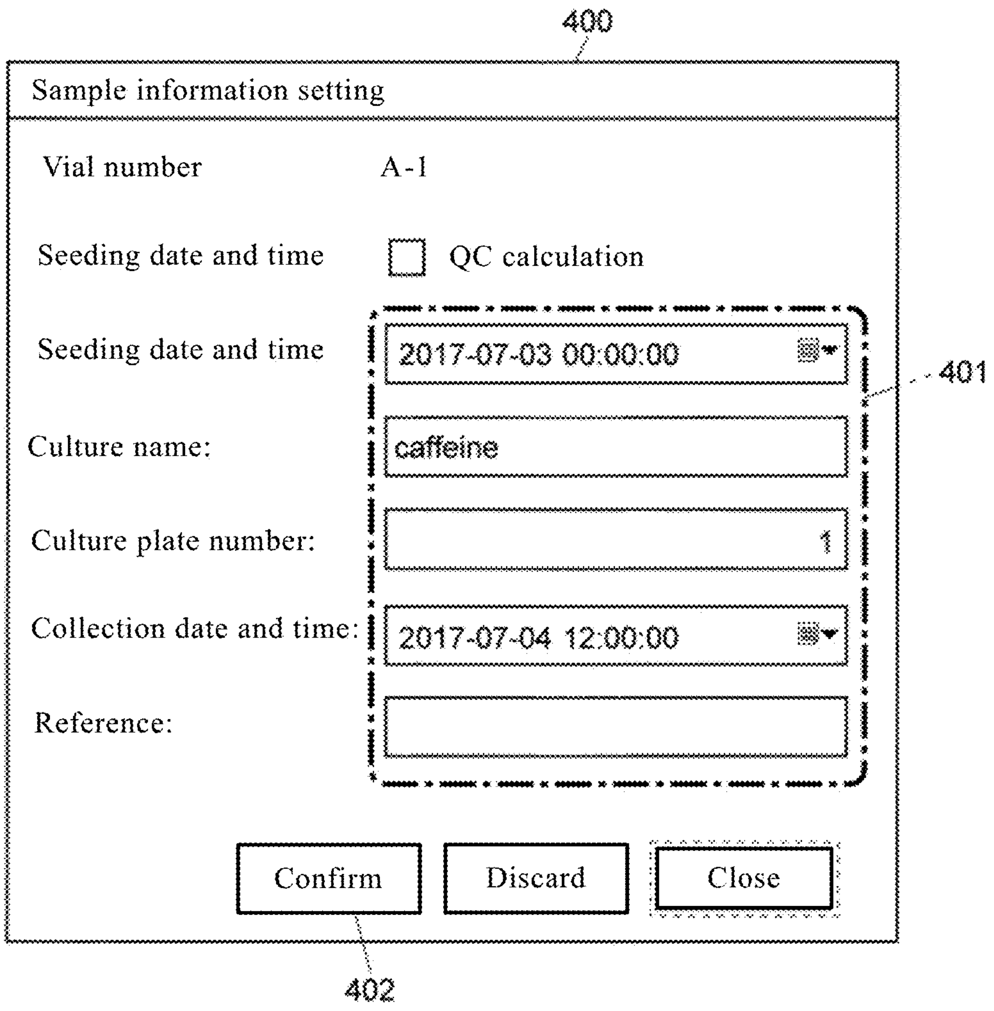
FIG. 3 is a diagram showing an example of a sample information setting screen in the culture medium sample automatic analysis system of this example.

When there is a vial whose sample information has not yet been set in the first sample arrangement image 111 on the device state confirmation screen 100 as shown in FIG. 2, the operator clicks a circular region 113 corresponding to a vial for which sample information is to be set with a pointing device included in the operation unit 7. Then, the display control unit 52 receives the operation, opens a new sample information setting screen 400 corresponding to the instructed vial number as shown in FIG. 3, and displays the newly opened sample information setting screen 400 on the screen of the display unit 8. FIG. 3 shows the case where a circular region 113 to which a vial number "A1" is assigned is instructed.

In this sample information setting screen 400, a text box 401 for inputting sample information, such as, e.g., a seeding date and time, a culture name, a culture plate number, a collection date and time, and a reference, is arranged. The reference is a value that is used as required when calculating and/or processing the analytical result, which will be described later, and can be an arbitrary value of, for example, the number of cells in the original culture vessel from which the culture medium sample was obtained, the lactate value (the quantity of substances produced when sugar is consumed), the concentration of bacteria, the absorbance of the culture solution, or the like, which is obtained by measuring or observing the results by another device not included in this system.

The operator inputs or selects appropriate information on the above-described items relating to sample information, and then clicks on the confirm button 402. Then, the input processing unit 53 receives this operation, determines the sample information for the vial number at that time, creates a sample information file including the sample information for each vial number, and stores the file in the setting information storage unit 55.

In the above procedures, the operator needs to input and set sample information for each vial, but it is also possible to collectively set sample information corresponding to a plurality of vials by creating a table in which sample information, such as, e.g., a seeding date and time, a culture name, a culture plate number, a collection date and time, and the like, is grouped in advance for a plurality of vials, i.e., a culture medium sample, and selecting a plurality of vials for which sample information has not been set and then selecting corresponding plurality of sample information on the above table.

Figure 4:
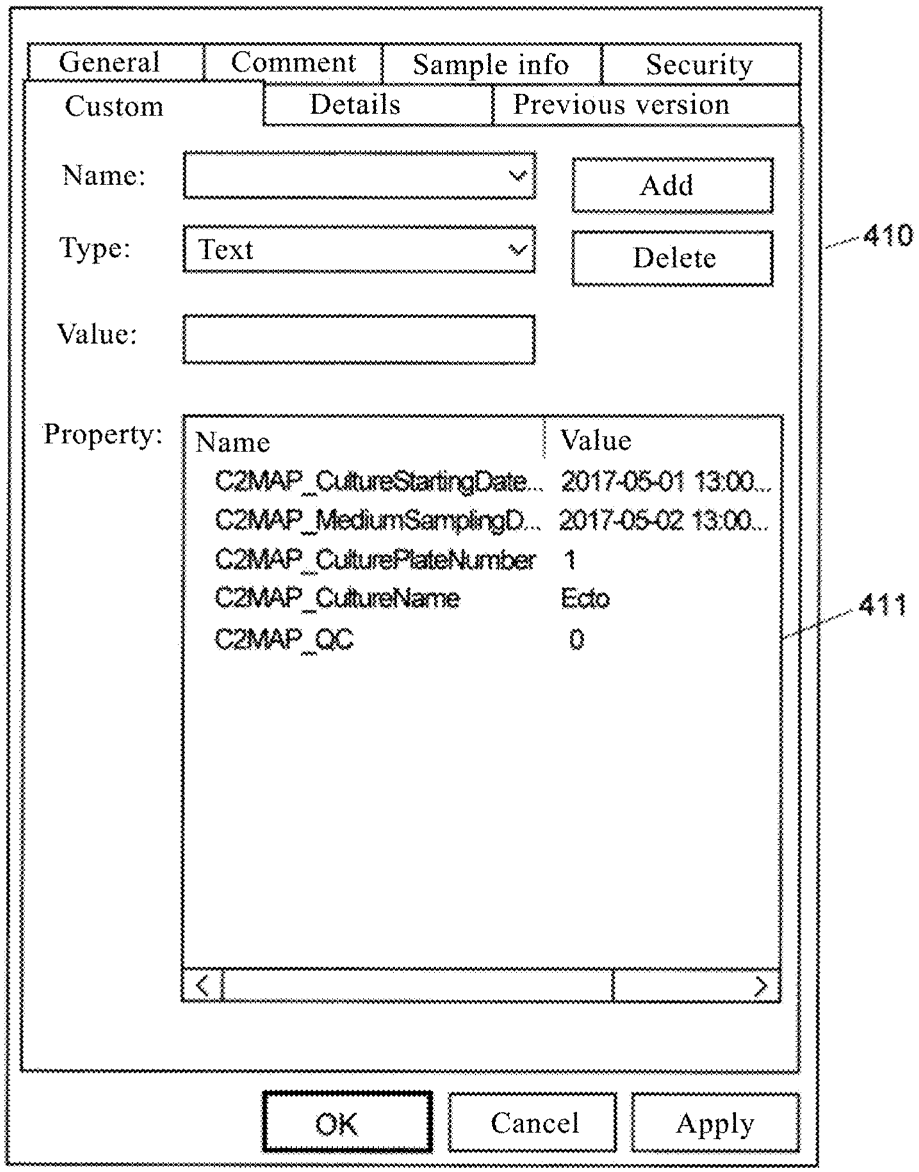
FIG. 4 is a diagram showing an example of property information of a culture medium sample in the culture medium sample automatic analysis system of this example.

As described above, the input processing unit 53 stores a sample information file including sample information in the setting information storage unit 55 for each vial, and at this time, the information of each item of the sample information is automatically registered in the custom property which is one of attribute information of the file. FIG. 4 is a diagram illustrating an example of a status in which sample information has been automatically registered in the custom property 411 on the file property dialogue screen 410. In this case, texts are set as the types of values of custom properties, and information on the seeding date and time, the collection date and time, the culture name, the culture plate number, and the QC value is registered as values corresponding to the names of "C2MAP_CultureStartingDate", "C2MAP_CultureSamplingDate", "C2MAP_CulturePlateNumber", "C2MAP_CultureName", and "C2MAP_QC", respectively.

As described above, the file including the sample information set for each vial in the control unit 5 is transferred to the data processing unit 4 at an appropriate time and stored in the sample information storage unit 40.

The data format of the file in which sample information is stored may vary from a manufacturer to a manufacturer of this system, but file properties can be shared on the same operating system base, e.g., Windows (registered trademark). Thus, for example, even when the manufacturer of the preprocessing device 2 constituting this system is different from the manufacturer of the LC-MS 3, and the data of the file in which sample information has been stored cannot be read data by the data processing unit 4 that processes data by the LC-MS 3, the sample information can be acquired using the properties of the file.

Next, the display mode of the analysis result after the analysis for a large number of culture medium samples is performed in this system will be described.

As described above, the data collected by analyzing a large number of culture medium samples by the LC-MS 3 is stored in the data storage unit 41. The quantitative analysis unit 42 uses the data to generate an extracted ion chromatogram for one or more given compounds per vial and calculates the area values of the peaks corresponding to the compounds. Further, a concentration value is calculated from the peak area value by referring to a calibration curve prepared in advance. Thereby, the peak area value and the concentration value of one or a plurality of compounds are obtained for each vial, that is, for each culture medium sample, and they are stored in the analysis result storage unit 43 as one file.

At this time, the file of the analytical result for each sample stored in the analysis result storage unit 43 is correlated with the file whose data is sample information of the same culture medium sample stored in the sample information storage unit 40. The data file of each sample stored in the data storage unit 41 is also correlated with the file of the sample information. As a result, for example, the analysis result file and/or the data file of the sample can be easily accessed from the sample information, and conversely, the sample information of the sample can be easily acquired from the analysis result file and/or the data file. As a result, the traceability related to the analysis can be appropriately managed.

Usually, in the culture medium assays in which this system is used, the culture supernatant in one culture vessel is continuously analyzed, for example, every day at the same time until the culture is completed, in order to evaluate the differentiation status of sample cells in culture. Therefore, culture medium samples to which the same culture name is attached are analyzed every day, and the data files and the analytical result files are created and stored, respectively. Since the amounts of compounds in culture medium samples derived from the same culture vessel (e.g. metabolites by cells) vary from day to day, observing this temporal change is crucial in the cell assessment. In this system, graphs based on analytical results are displayed in association with sample information in the following manner.

Figure 5:
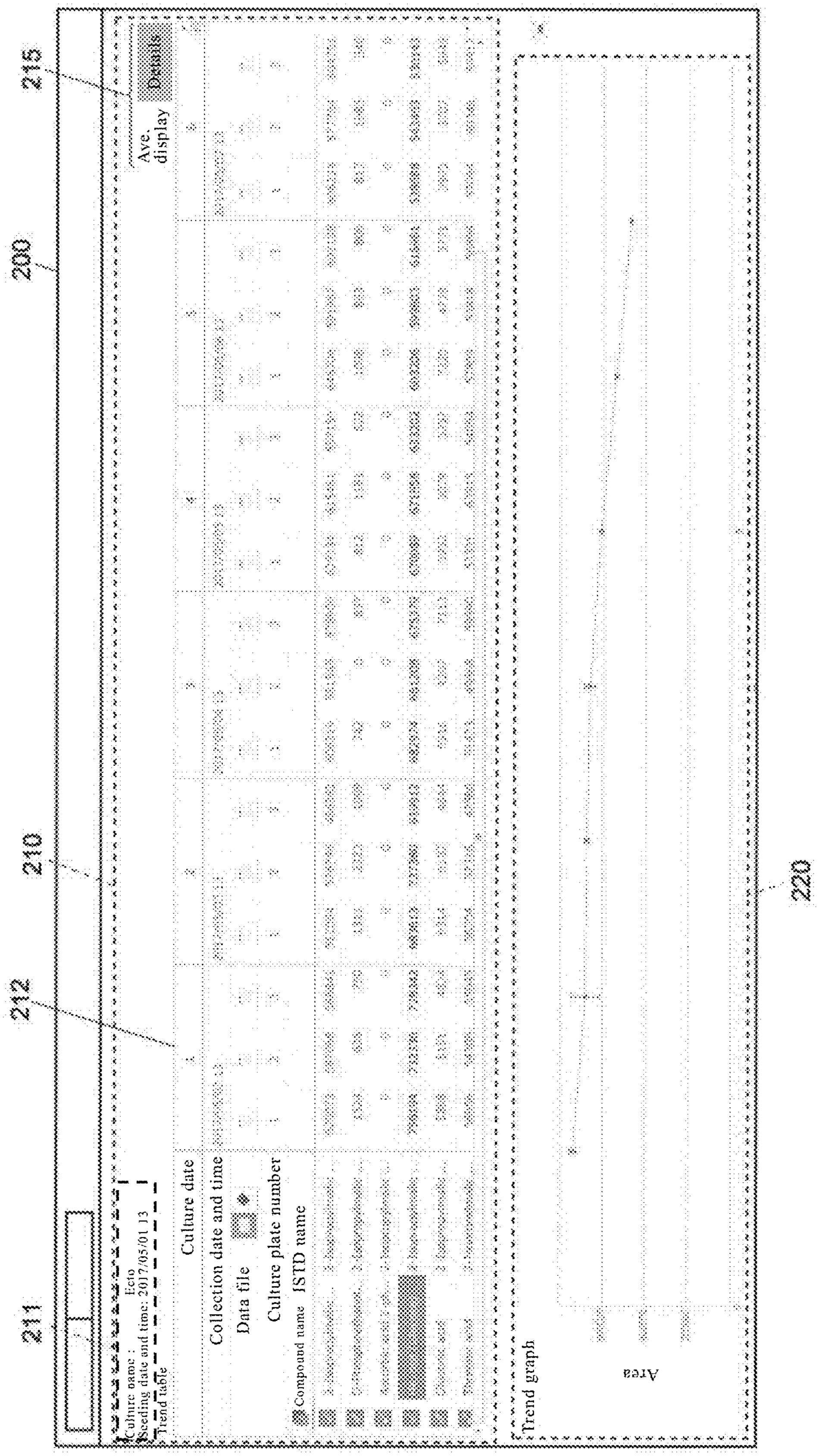
FIG. 5 is a diagram showing an example of an analysis result display screen (main screen) in the culture medium sample automatic analysis system of this example.
Figure 6:
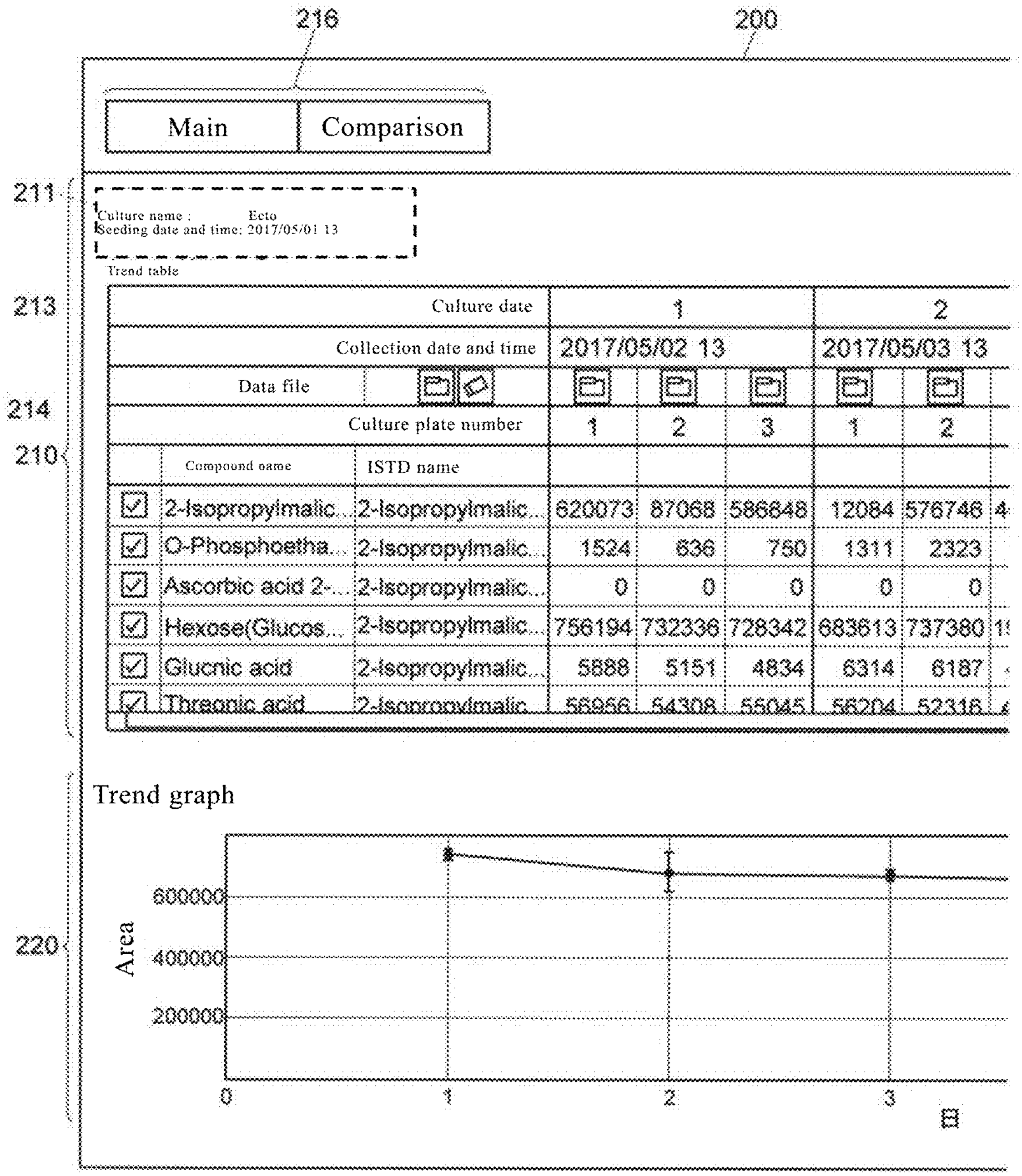
FIG. 6 is a diagram showing a left part of the analysis result display screen shown in FIG. 5.

That is, when an operator performs a predetermined manipulation after designating a culture name or the like in the operation unit 7, the result display processing unit 44 reads the file of the sample information corresponding to the designated information and the analytical result file from the sample information storage unit 40 and the analysis result storage unit 43, creates a main analysis result display screen 200 as shown in FIG. 5 and FIG. 6 based on the data in the file and displays the screen on the display unit 8. FIG. 5 is a diagram showing the entire main analysis result display screen 200, and FIG. 6 is a diagram showing a left part of the main analysis result display screen 200. The main analysis result display screen 200 is divided roughly into two parts upward and downward, and a table display region 210 is provided upward and a graph display region 220 is provided downward.

In the upper left part of the table display region 210, a sample information display region 211 for displaying a culture name as sample information and a seeding date and time is provided, and a trend table 212 is disposed below the sample information display region 211. The trend table 212 is a table in which the types of compounds (metabolites) to be analyzed are arranged in the vertical direction, and culture plate numbers for the culture date (number of days elapsed from the initiation of culture) and the collection date and time are arranged in the horizontal direction. In this example, the number of culture vessels (culture plates) cultured under the same condition is three, so the culture plate number is only 1 to 3, but this number can be further increased.

In the respective cells of the trend table 212, a quantitative value for one culture plate number of a certain type of compound on a certain culture date is displayed. The quantitative value referred to here is a peak area value, the area ratio to a peak area value under a specific condition (for example, the area ratio when the area value on the first day of the collection date and time is set to 1), a concentration value, the concentration ratio to a concentration value under a specific condition (for example, the concentration ratio when a concentration value on the first day of the collection date and time is set to 1), or any of the calculated values obtained by dividing these values by the above-mentioned reference value. Which value is to be displayed as the quantitative value can be appropriately selected by an operator in another setting screen, but in any case, the analytical result calculated for each compound by the quantitative analysis unit 42 is displayed here.

A detailed mode/average display mode selection button 215 is provided at the upper right portion of the table display region 210. FIG. 5 and FIG. 6 show a state in which the detailed mode is selected by the button 215, and in this state, all the results of three samples having different culture plate numbers at the same collection date and time are displayed. On the other hand, when the average display mode is selected by the detailed mode/average display mode selection button 215, the result display processing unit 44 averages the results of three samples having different culture plate numbers at the same collection date and time for each compound, and displays the average values in the trend table 212. Even if cultured under the same conditions, it is inevitable that a difference occurs in the cell proliferation and the like, and the results of the three samples at the same collection date and time have a certain degree of discrepancy; therefore, usually, only the average value is confirmed by the average display mode. However, if the result is questionable, the presence or absence of abnormal values can be confirmed by confirming the individual peak area value and/or the concentration value by selecting the detailed display mode.

In the graph display region 220 of the main analysis result display screen 200, a graph (trend graph) indicating a change in peak area value or the like of one compound selected in the trend table 212 is displayed. When the operator specifies a compound whose trend graph is desired to be confirmed by the operation unit 7 on the trend table 212, the result display processing unit 44 collects the analytical results for the indicated compound and generates the trend graph to update the display in the graph display region 220. In the example of FIG. 5, "Hexose (Glucose)" in the fourth line of the trend table 212 is selected, and the trend graph indicating the change in the peak area value with respect thereto is displayed. The value on the graph is an average for three samples with different culture plate numbers at the same collection date and time, and the variations in the value are indicated by error bars. The value used for this error bar display can be selected by the operator from among variances, standard deviations, etc. in a different setting screen.

When the variation of the error bar displayed value is too large, there is a high possibility that some abnormality has occurred. Therefore, a threshold value for an error may be specified by a different setting screen by an operator, and when the error exceeds this threshold value, an operator may be warned that the degree of the error is abnormal by displaying the error bar in a display color different from the normal display color or the like.

In the main analysis result display screen 200, only a trend graph for one specified culture name can be confirmed. However, in cases where it is desired to compare the results of a plurality of culture medium samples different in culture name, the operator selects the comparison mode with the main mode/comparison mode selection button 216 displayed at the uppermost portion of the main analysis result display screen 200. Then, the result display processing unit 44 displays a comparison analysis result display screen 300 as shown in FIG. 7 on the display unit 8.

Figure 7:
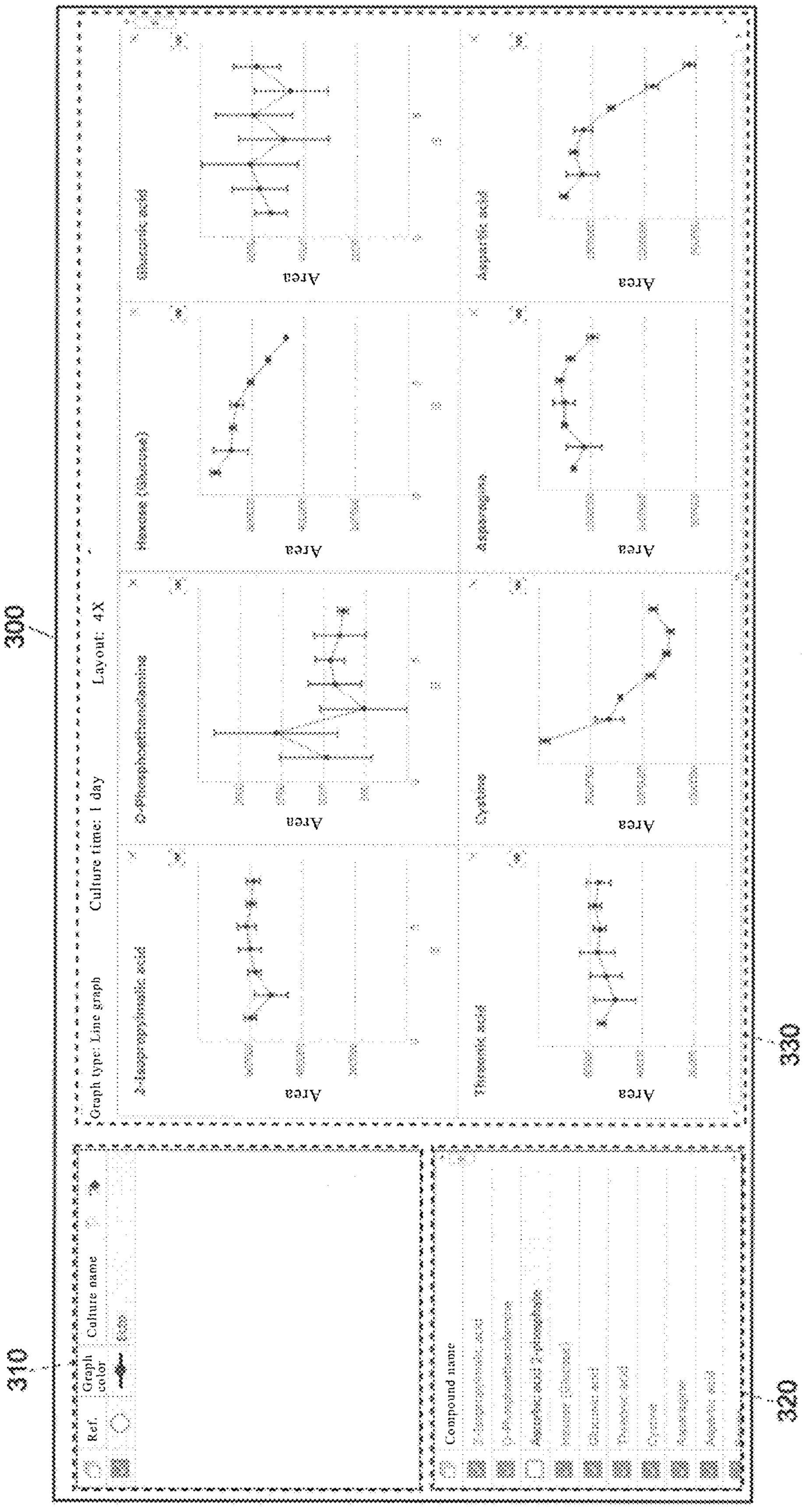
FIG. 7 is a diagram showing an example of an analysis result display screen (comparison screen) in the culture medium sample automatic analysis system of this example.
Figure 8:
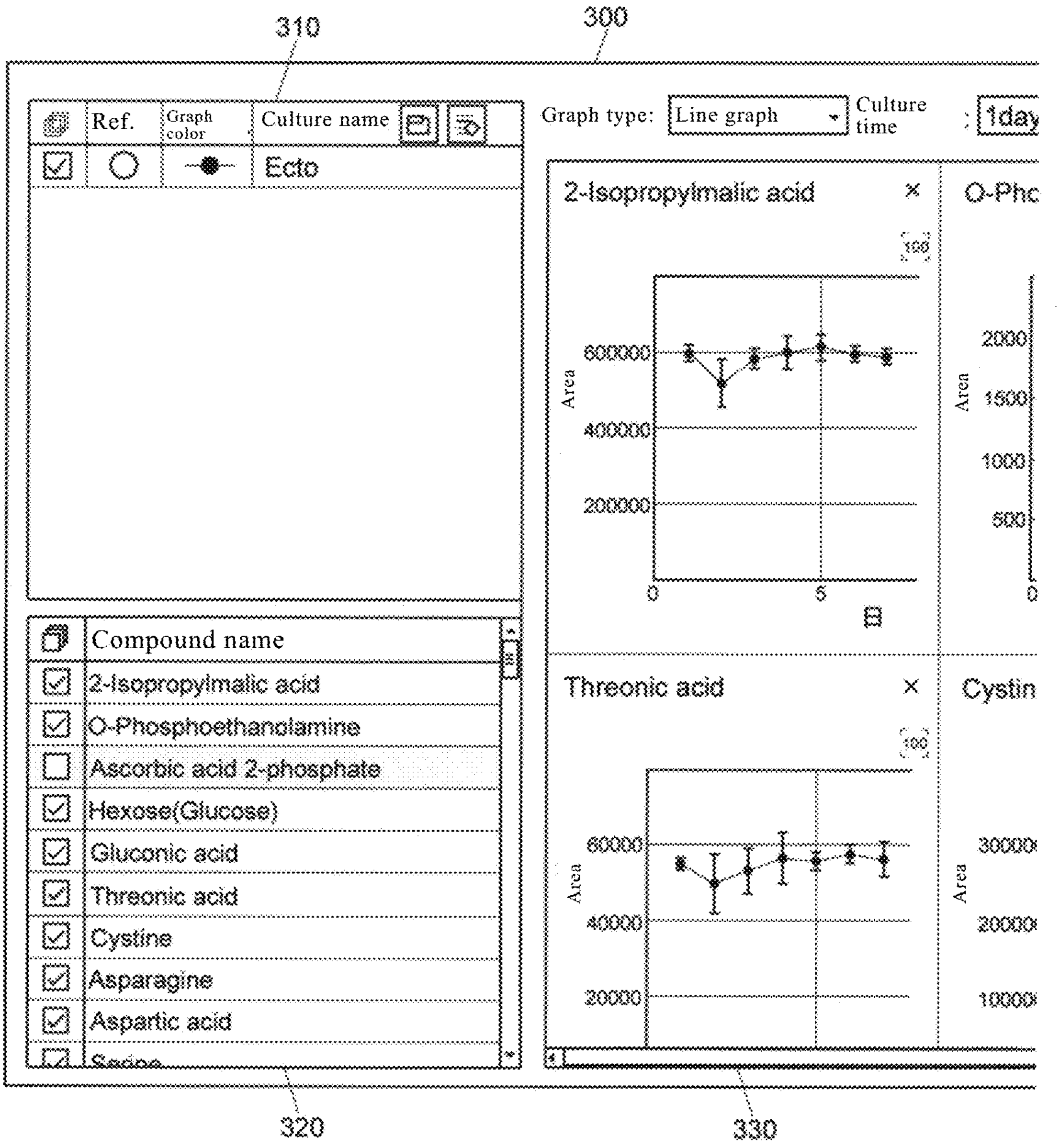
FIG. 8 is a diagram showing a left part of the analysis result display screen shown in FIG. 7.

FIG. 7 is a diagram showing the entire comparison analysis result display screen 300, and FIG. 8 is a diagram showing a left side part of the comparison analysis result display screen 300. The comparison analysis result display screen 300 is generally divided into three regions. A sample type table display region 310 is provided at the upper left, a compound table display region 320 is provided at the lower left, and a graph display region 330 is provided at the right. A sample type table having one culture name as one line is displayed in the sample type table display region 310, and a compound table having one compound as one line is displayed in the compound table display region 320. A check box is provided in each row of the sample type table and the compound table, and a trend graph which is an analyzed result obtained by checking the check box is displayed in the graph display region 330.

In the example of FIG. 7 and FIG. 8, trend graphs of the compounds other than the ascorbic acid 2-phosphate for the culture medium sample whose culture name is "Ecto" is displayed in the graph display region 330. The trend graph per se is the same as that displayed in the graph display region 220 of the main analysis result display screen 200, and averages and error bars, such as the peak area values and the concentration values, are displayed for each collection day. This makes it possible to easily compare temporal changes such as peak area values of different compounds.

Figure 9:
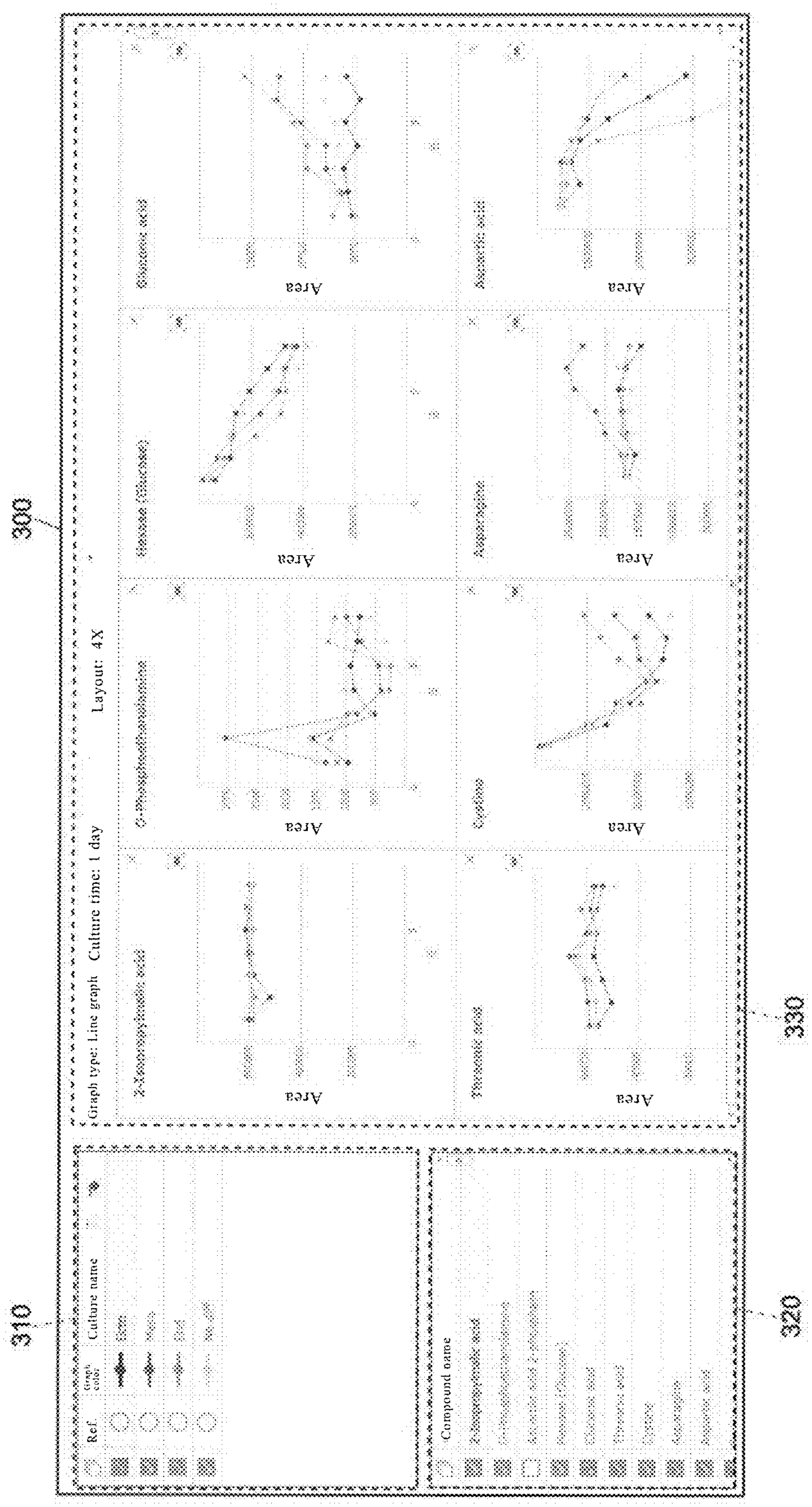
FIG. 9 is a diagram showing an example of an analysis result display screen (comparison screen) in the culture medium sample automatic analysis system of this example.
Figure 10:
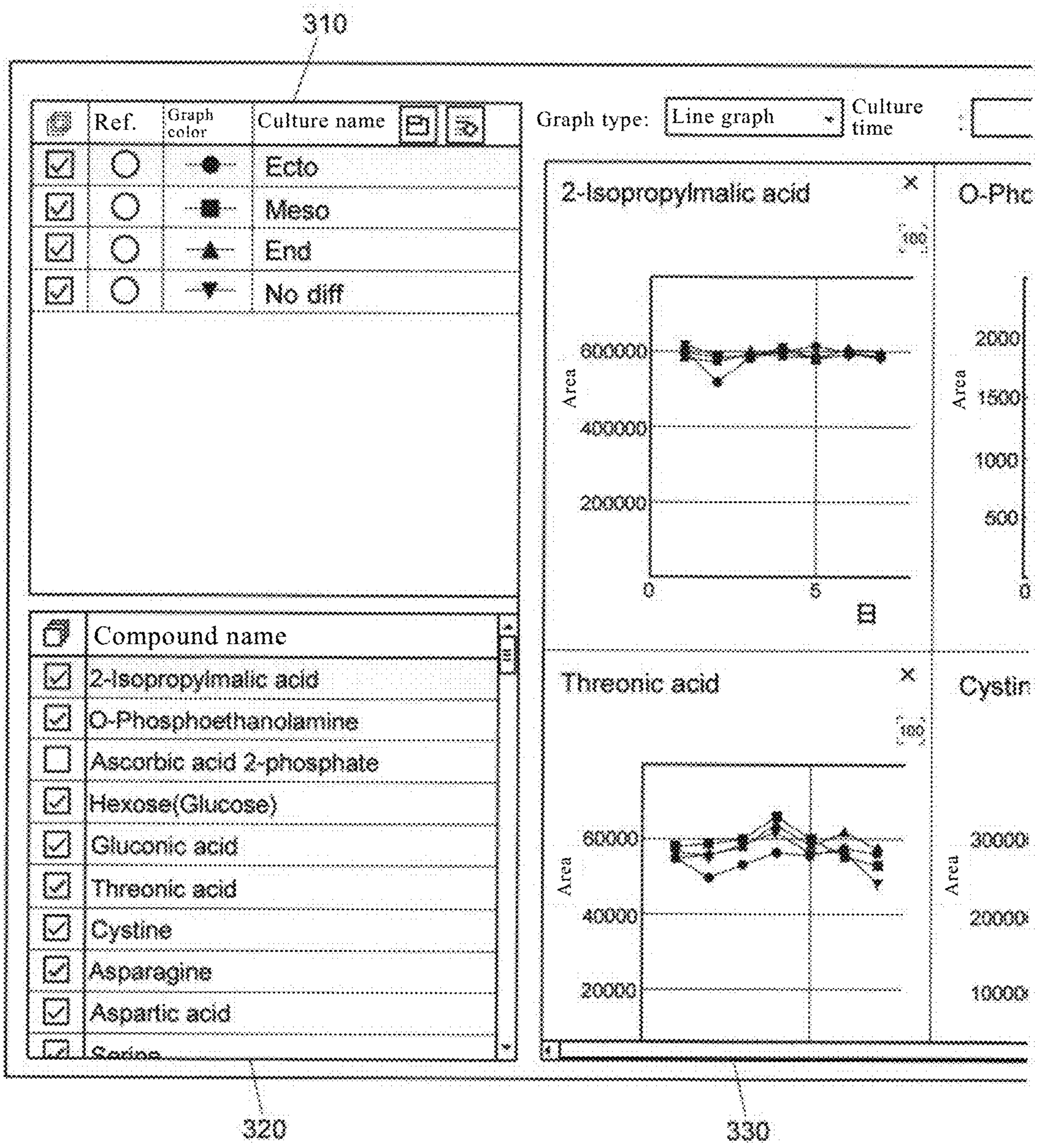
FIG. 10 is a diagram showing a left part of the analysis result display screen shown in FIG. 9.

It is also possible to compare the analytical results of culture medium samples, which are different culture names, in the comparison analysis result display screen 300. That is, when an operator designates a plurality of culture names to be compared in the another setting screen, the result display processing unit 44 displays a comparison analysis result display screen 300 as shown in FIG. 9 and FIG. 10 on the display unit 8. FIG. 9 is a diagram showing the entire comparison analysis result display screen 300, and FIG. 10 is a diagram showing a left side portion of the comparison analysis result display screen 300. At this time, a sample type table in which a plurality of designated culture names is listed is displayed in the sample type table display region 310. Different graph colors are assigned to each culture name. Note that, here, since the color cannot be shown, the shape of plot points on the graph is differentiated.

Then, a trend graph in which line graphs corresponding to different samples having different culture names are superimposed is displayed in the graph display region 330. In the examples of FIG. 9 and FIG. 10, trend graphs of compounds other than Ascorbic acid 2-phosphate for four types of culture medium samples whose culture names are "Ecto", "Meso", "End", and "No diff" are displayed in the graph display region 330. This makes it possible to easily compare changes in quantitative values of the same compound in different cultured cells.

Figure 11:
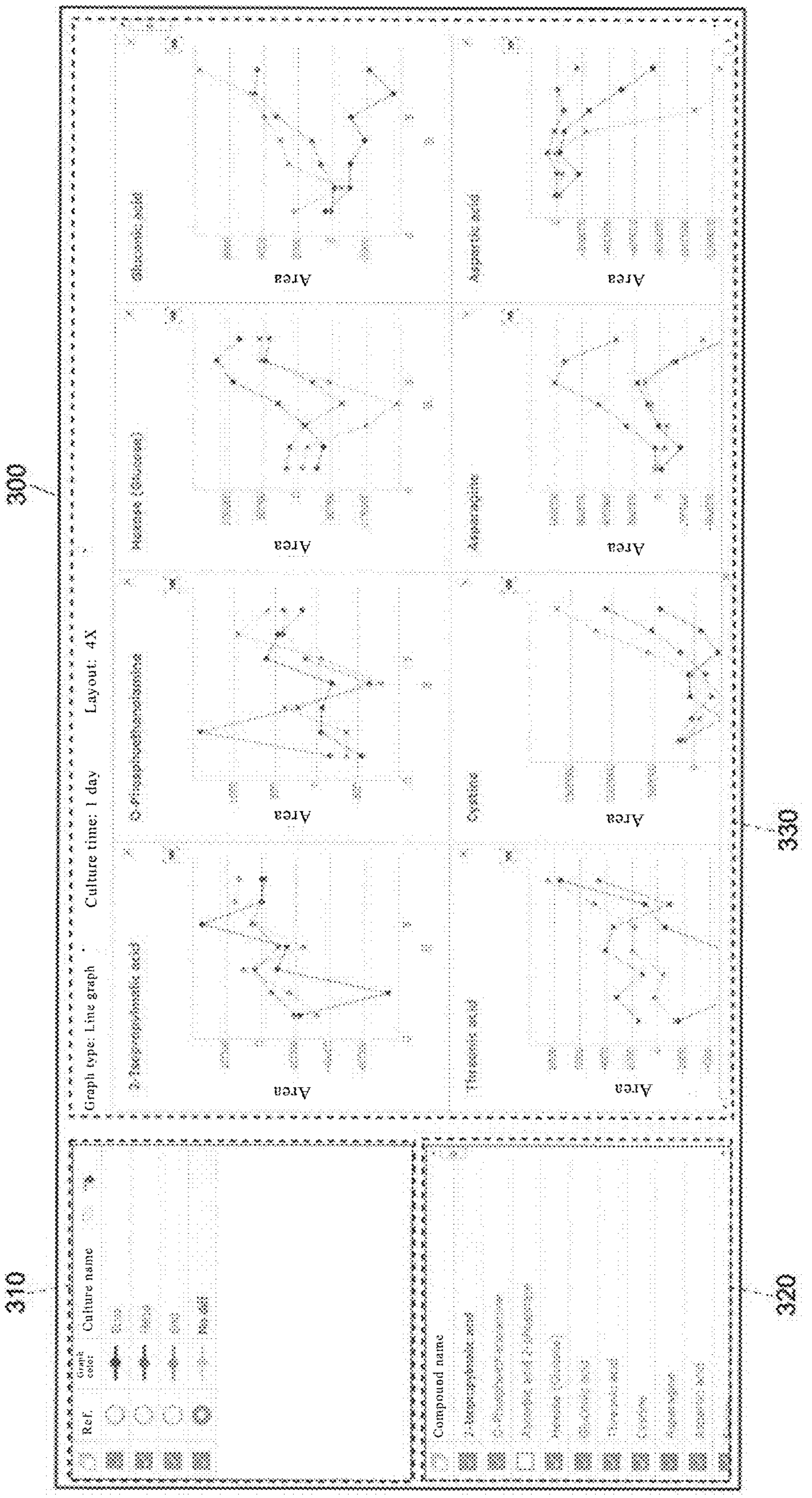
FIG. 11 is a diagram showing an example of an analysis result display screen (comparison screen) in the culture medium sample automatic analysis system of this example.
Figure 12:
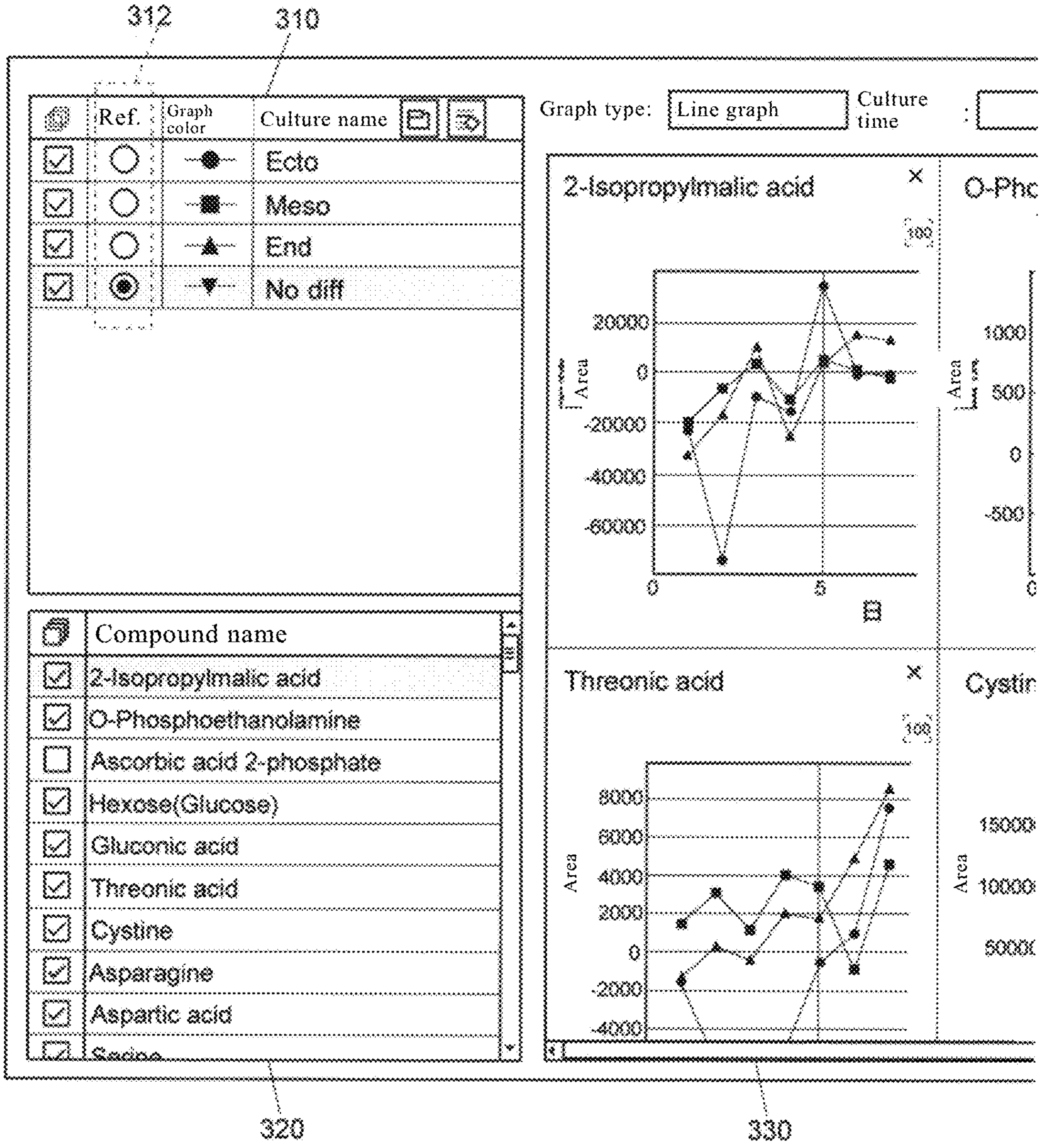
FIG. 12 is a diagram showing a left part of the analysis result display screen shown in FIG. 11.

Furthermore, any one of a plurality of culture medium samples may be used as a reference, and differences between the analysis result of the reference and other analysis results may be displayed. That is, as shown in FIG. 11 and FIG. 12, when an operator checks the reference radio button 312 of a row corresponding to one sample to be used as a reference on the sample type table displayed in the sample type table display region 310, the result display processing unit 44 calculates, for each compound, the difference between the peak area value or concentration value in the reference sample and the peak area value or concentration value in the other sample, and creates a trend graph indicating the temporal change of the difference. Then, a trend graph is displayed on the graph display region 330.

In the examples of FIG. 11 and FIG. 12, the culture medium sample whose culture name is "No diff" is used as a reference, and a trend graph of compounds other than Ascorbic acid 2-phosphate for the other three types of samples is displayed in the graph display region 330. In this trend graph, it is possible to more intuitively grasp the change in the difference between the quantitation value and the reference value.

It should be noted that the above examples are examples of the present invention, and it is needless to say that the scope of the present invention may be appropriately changed, modified, or added to encompass the claims.

For example, in the system of the above examples, the number of vials mountable in the sample placement section 20 and 302 may be changed as appropriate, and the shape of the rack on which vials are mounted in the sample placement section 20 and 302 may also be changed as appropriate. In addition, the method of applying the vial number can be changed as appropriate.

Although the above examples are directed to a system of analyzing a compound such as a metabolite contained in a culture medium sample by an LC-MS, a compound in a sample derived from another living body of a culture medium sample may be analyzed. The analysis device is not limited to an LC-MS, and may be a GC-MS, or may be an analysis device, such as, e.g., another optical analysis device. As described above, the preprocessing by the preprocessing device is not limited to removing proteins or other undesirable components and may be various preprocessing. Further, in the system of the above examples, the dilution of a sample is carried out by an auto-sampler in an LC-MS, but the dilution may be carried out by a preprocessing device.

DESCRIPTION OF SYMBOLS

1 . . . Culture device
2 . . . Preprocessing device
20 . . . Sample placement section
21 . . . Preprocessing execution unit
22 . . . Sample delivery unit
3 . . . LC-MS
30 . . . Auto-sampler
301 . . . Sample dilution unit
302 . . . Sample placement section
303 . . . Sampling unit
31 . . . LC unit
32 . . . MS unit
4 . . . Data processing unit
40 . . . Sample information storage unit
41 . . . Data storage unit
42 . . . Quantitative analysis unit
43 . . . Analysis result storage unit
44 . . . Result display processing unit
5 . . . Control unit
50 . . . Preprocessing execution control unit
51 . . . LC-MS execution control unit
52 . . . Display control unit
53 . . . Input processing unit
54 . . . Vial number management unit
55 . . . Setting information storage unit
6 . . . Main control unit
7 . . . Operation unit
8 . . . Display unit
100 . . . Device state confirmation screen
110 . . . Preprocessing state display region
111 . . . First sample arrangement image
112 . . . Arcuate region
113, 122 . . . circular region
120 . . . Analysis state display region
121 . . . Second sample arrangement image
114, 123 . . . operating state display unit
130 . . . Start button
131 . . . Pause button
132 . . . Stop button

The invention claimed is:

1. An automatic analysis system for performing predetermined preprocessing on a plurality of samples and then performing a predetermined analysis on the plurality of samples that has been preprocessed, the system comprising:

a) a preprocessing device configured to perform the predetermined preprocessing on the plurality of samples;

b) an analysis device configured to perform the predetermined analysis on the plurality of samples that have been preprocessed; and c) a controller, wherein the preprocessing device comprises a first sample placement section on which a first plurality of sample containers each containing one of the plurality of samples is placed, and performs the predetermined preprocessing on one of the plurality of samples contained in one of the first plurality of sample containers placed in the first sample placement section, wherein the analysis device comprises:

a second sample placement section on which a second plurality of sample containers each containing one of the plurality of samples that has been preprocessed is placed;

a sampling unit; and a measurement unit, wherein the controller controls the sampling unit so as to collect one of the plurality of samples that has been preprocessed by a predetermined amount from one of the second plurality of sample containers and introduce the collected sample into the measurement unit, wherein the measurement unit is configured to perform the predetermined analysis on the sample introduced by the sampling unit, wherein the controller allocates an identical number to a first sample placement position and a second sample placement position, the first sample placement position being a vial position defined on the first sample placement section, at which one of the first plurality of sample containers is placed, and the second sample placement position being a vial position defined on the second sample placement section, at which one of the second plurality of sample containers is placed, wherein the controller displays a first sample arrangement image and a second sample arrangement image, the first sample arrangement image showing an arrangement of the first plurality of sample containers in the first sample placement section with a first plurality of display regions corresponding thereto, the second sample arrangement image showing an arrangement of the second plurality of sample containers in the second sample placement section with a second plurality of display regions corresponding thereto, wherein the controller displays the identical number in association with one of the first plurality of display regions and one of the second plurality of display regions respectively, and wherein one of the plurality of samples that has been preprocessed is delivered from the first sample placement position to the second sample placement position, with the identical number allocated by the controller.

2. The automatic analysis system as recited in claim 1, wherein the controller is configured to receive information indicating a state of progress of respective operations from the preprocessing device and the analysis device and change a display mode in one of the first plurality of display regions and a display mode in one of the second plurality of display regions, according to the state of progress.

3. The automatic analysis system as recited in claim 2, wherein the controller is further configured for a user to identify one or more of the first plurality of display regions, and wherein the controller is further configured to display an input setting screen which allows the user to input sample information of a sample from among the plurality of samples accommodated in one of the first plurality of sample containers associated with the one or more of the first plurality of display regions when the one or more of the first plurality of display regions are identified via the controller, and wherein the automatic analysis system further comprises a sample information storage unit configured to store the sample information input by an operation of the user on the input setting screen displayed by the controller in association with the number allocated.

4. The automatic analysis system as recited in claim 3, wherein the controller is configured to change the display mode of the first plurality of display regions depending on whether or not the sample information has been set.

5. The automatic analysis system as recited in claim 1, wherein a shape of an envelope of the first plurality of display regions is different from a shape of an envelope of the second plurality of display regions.

6. The automatic analysis system as recited in claim 1, wherein the number allocated is a vial number.

7. The automatic analysis system as recited in claim 1, wherein the controller displays the first sample placement position and the second sample placement position, which have been allocated the identical number, in a manner different from that used for a third sample placement position and a fourth sample placement position, the third sample placement position being a vial position defined on the first sample placement section, at which another one of the first plurality of sample containers is placed, and the fourth sample placement position being a vial position defined on the second sample placement section, at which another one of the second plurality of sample containers is placed.

8. The automatic analysis system as recited in claim 1, wherein the measurement unit includes a chromatograph.

* * * * *